United States Patent
Kim et al.

(10) Patent No.: US 9,332,762 B2
(45) Date of Patent: May 10, 2016

(54) METHOD FOR PREPARING AMICARBAZONE

(71) Applicant: KS LABORATORIES CO., LTD., Suncheon (KR)

(72) Inventors: Keun Sik Kim, Suncheon (KR); Yeon Tak Choi, Suncheon (KR)

(73) Assignee: KS LABORATORIES CO., LTD., Suncheon (KR)

( * ) Notice: Subject to any disclaimer, the term of this patent is extended or adjusted under 35 U.S.C. 154(b) by 0 days.

(21) Appl. No.: 14/761,594

(22) PCT Filed: Jan. 22, 2014

(86) PCT No.: PCT/KR2014/000604
§ 371 (c)(1),
(2) Date: Jul. 16, 2015

(87) PCT Pub. No.: WO2014/116012
PCT Pub. Date: Jul. 31, 2014

(65) Prior Publication Data
US 2015/0336906 A1    Nov. 26, 2015

(30) Foreign Application Priority Data

Jan. 25, 2013 (KR) ........................ 10-2013-0008417

(51) Int. Cl.
*C07D 249/12* (2006.01)
*A01N 47/38* (2006.01)
*C07C 271/08* (2006.01)
*C07C 269/04* (2006.01)

(52) U.S. Cl.
CPC .............. *A01N 47/38* (2013.01); *C07C 269/04* (2013.01); *C07C 271/08* (2013.01); *C07D 249/12* (2013.01)

(58) Field of Classification Search
CPC .................................................... C07D 249/12
See application file for complete search history.

(56) References Cited

U.S. PATENT DOCUMENTS 5,856,495 A    1/1999    Weckbecker et al.
2008/0171662 A1    7/2008    Gesing et al.

FOREIGN PATENT DOCUMENTS

WO    WO 2011/148922 A1    12/2011

OTHER PUBLICATIONS

Yan-Ping Luo et al., "Syntheses and Herbicidal Activities of Novel Triazolineone Derivatives," Journal of Agricultural and food Chemistry, 2008, pp. 2118-2134, vol. 56, No. 6.
International Search Report for PCT/KR2014/000604 filed on Jan. 22, 2014.

*Primary Examiner* — Michael Barker
*Assistant Examiner* — Karen Cheng

(57) ABSTRACT

The present invention relates to a method for preparing amicarbazone by using amino-triazolinone, which is an intermediate compound, and relates to a method for preparing amicarbazone, comprising the steps of: obtaining hydrazine carboxylic acid represented by 5 chemical formula (V) by reacting acylhydrazide represented by chemical formula (II) and a carbamating agent represented by chemical formula (III) or (IV); reacting the obtained hydrazine carboxylic acid represented by chemical formula (V) and hydrazine hydrate in the presence of a base catalyst; and reacting the obtained compound represented by chemical formula (I) 10 and an alkyl isocyanate represented by chemical formula (IV) in the presence of a base catalyst. Amino-triazolinone and amicarbazone would be stably produced by the present invention without safety gear and safety facilities for the leakage of phosgene, which has been conventionally used as a reactant.

7 Claims, 6 Drawing Sheets

METHOD FOR PREPARING AMICARBAZONE

TECHNICAL FIELD

The present invention relates to a method for preparing amicarbazone, which is a triazolinone-based herbicidal active compound represented by Formula VII, using amino-triazolinone represented by Formula I as an essential intermediate compound.

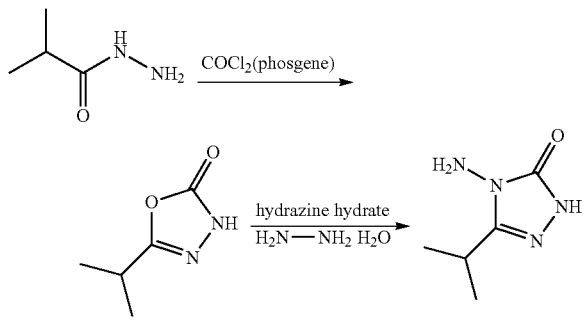

The compound (I) is a white powder having the chemical name 3-isopropyl-4-amino-1,2,4-triazol-5-one (or 3H-1,2,4-triazol-3-one) and a melting point of 168° C. to 176° C. Amino-triazolinone is an essential raw material of amicarbazone represented by Formula VII and is used as an herbicide for crops such as sugar cane, corn, and the like.

BACKGROUND ART

Amino-triazolinone according to the present invention is prepared using hydrazine as a starting raw material and poisonous phosgene as an intermediate material, as shown in the following Reaction Formula. Such a process was first developed by Bayer AG in Germany and produces amicarbazone, which is a prominent plant growth regulator. Amicarbazone is mainly used in large farms producing sugar cane and corn, and with increasing demand for sugar cane as a raw material for bioethanol and a raw material for raw sugar, demand for herbicides is also increasing.

Although methods for preparing amino-triazolinone have been registered as patents since the amino-triazolinone of the present invention was publicly known in the art (see J. Heterocyclic Chem., 21(6), 1769-74 (1984)), most of these patents relate to a method for preparing amino-triazolinone using phosgene. Representative inventions using phosgene are disclosed in detail in U.S. Pat. No. 4,952,701 (filed in 1988), U.S. Pat. No. 5,693,821 (filed in 1996) and U.S. Pat. No. 5,912,354 (filed in 1998), and examples of inventions relating to amicarbazone are disclosed in detail in U.S. Pat. No. 5,194,085 (filed in 1991) and U.S. Pat. No. 5,625,073 (filed in 1995) (see the published patent documents for details).

DISCLOSURE

Technical Problem

As can be seen from the method for preparing amino-triazolinone known in the art, dangerous phosgene gas is used in the method. As is well known in the art, since the phosgene gas is poisonous, leakage of phosgene gas poses a fatal health hazard and application thereof entails inherent risk. In addition, since amino-triazolinone is prepared at a high temperature of 70° C. to 80° C. or higher in a phosgenation reaction, the high-temperature reaction with the phosgene which is a gas at room temperature is very dangerous (U.S. Pat. No. 5,756,752 (filed in 1997).

Further, increase in equipment investment due to supplementation of safety equipment or safety facilities for preventing leakage of the poisonous phosgene gas also causes increase in preparation costs of amino-triazolinone and amicarbazone, which is the final product of the amino-triazolinone to be prepared in the method according to the present invention, whereby the price competitiveness of the final product is decreased, thereby decreasing cost competitiveness as compared with other herbicides.

Therefore, there is a need for development of a process capable of stably preparing amino-triazolinone which is an essential raw material of amicarbazone, which is an herbicide as a plant growth regulator. In addition, there is a need for development of an additional process capable of preparing amicarbazone as a final product using the prepared amino-triazolinone while decreasing preparation costs of the amino-triazolinone.

Technical Solution

The above and other objects of the present invention can be achieved by the following preparation method.

Embodiments of the present invention provide a method for preparing amicarbazone of Formula VII, which includes: (1) reacting acyl hydrazide of Formula II with a carbamating agent of Formula III to obtain hydrazine carboxylic acid of Formula V; (2) reacting the obtained hydrazine carboxylic acid of Formula V with hydrazine hydrate in the presence of a base catalyst to obtain a compound of Formula I; and (3) reacting the obtained compound of Formula I with t-butyl isocyanate of Formula VI in the presence of a base catalyst to prepare amicarbazone of Formula VII.

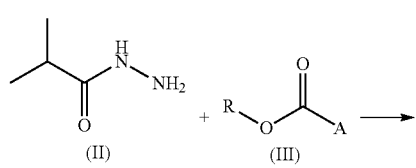

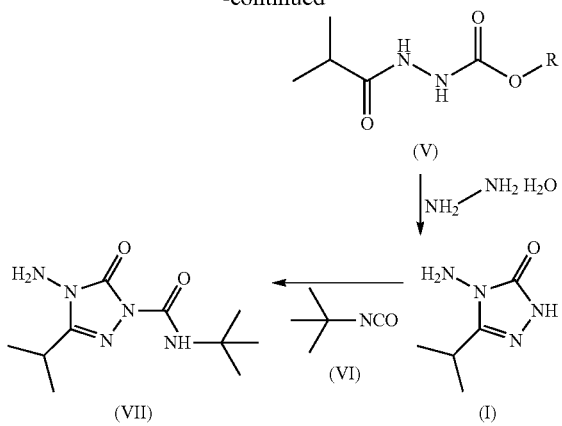

(wherein A is Cl, F, Br, or OR, and R is a $C_1$ to $C_{12}$ alkyl group or aryl group.)

The carbamating agent may be a dialkyl carbonate such as dimethyl carbonate, diethyl carbonate, and the like, and may include any one selected from the group consisting of methyl chloroformate, ethyl chloroformate, and isopropyl chloroformate.

The base may be any one selected from the group consisting of LiOH, NaOH, KOH, LiHCO$_3$, Li$_2$CO$_3$, NaHCO$_3$, Na$_2$CO$_3$, KHCO$_3$, K$_2$CO$_3$, and CaCO$_3$.

The carbamating agent of Formula III used in step (1) may be methyl chloroformate (MCF); a solvent used in step (1) may be selected from among methylene chloride (MC), methanol and toluene; and a reaction temperature in step (1) may range from 10° C. to 25° C.

The base used in step (2) may be NaOH or KOH; a solvent used in step (2) may be toluene; and a reaction temperature in step (2) may range from 90° C. to 100° C. The base catalyst used in step (3) may be LiOH, NaOH, or KOH as well as amine salts such as 1,8-diazabicyclo[5.4.0]undec-7-ene (DBU), and a reaction temperature in step (3) may range from 50° C. to 80° C.

Embodiments of the present invention provide a new intermediate compound of Formula V, which is usefully used as an intermediate material in the preparation method according to the present invention. Further, embodiments of the present invention provide a method for preparing hydrazine carboxylic acid of Formula V as an intermediate compound by reacting acyl hydrazide of Formula II with a carbamating agent of Formula III.

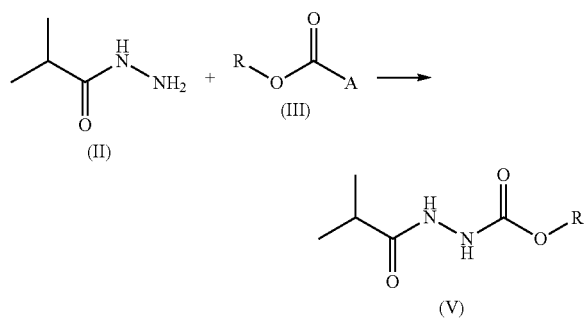

(wherein R is a $C_2$ to $C_{12}$ alkyl group or aryl group.)

Advantageous Effects

According to the present invention, amino-triazolinone as an intermediate and amicarbazone as a final product may be stably prepared without using safety equipment or safety facilities for preventing leakage of phosgene which has been used as a conventional reactant. Therefore, preparation costs of amicarbazone can be decreased to increase price competitiveness of the final product and to increase cost competitiveness as compared with other herbicides.

BEST MODE

Figure 1:
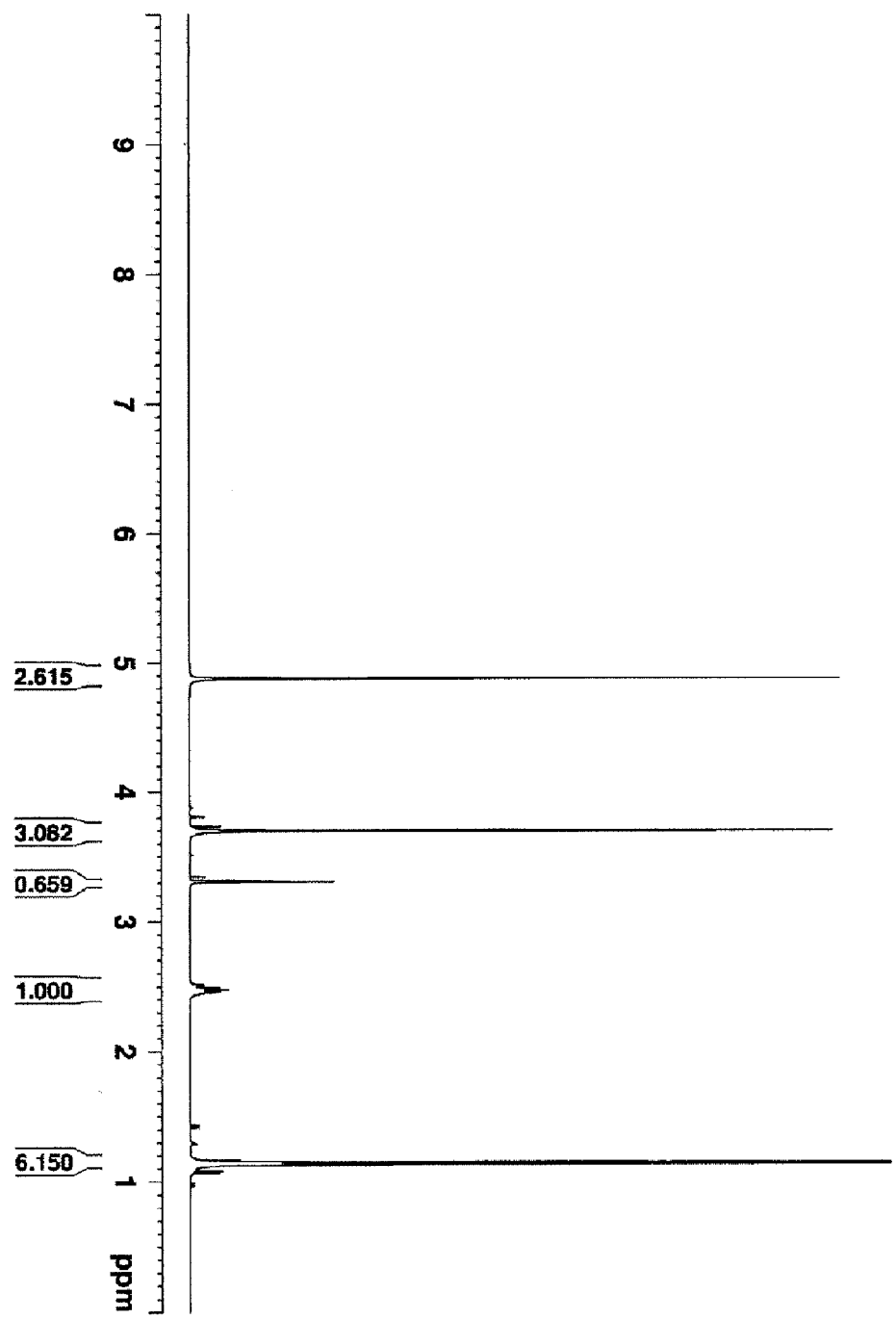
FIG. 1 is a graph depicting H-NMR data of a product obtained in Example 1.

According to the following Reaction Formula, a preparation method according to the present invention may include three steps, that is, step (1) of reacting acyl hydrazide of Formula II with a carbamating agent of Formula III to prepare hydrazine carboxylic acid of Formula V; step (2) of reacting the obtained hydrazine carboxylic acid of Chemical Formula V with hydrazine hydrate to prepare amino-triazolinone of Formula I; and step (3) of reacting the obtained amino-triazolinone of Formula I with t-butyl isocyanate of Formula VI:

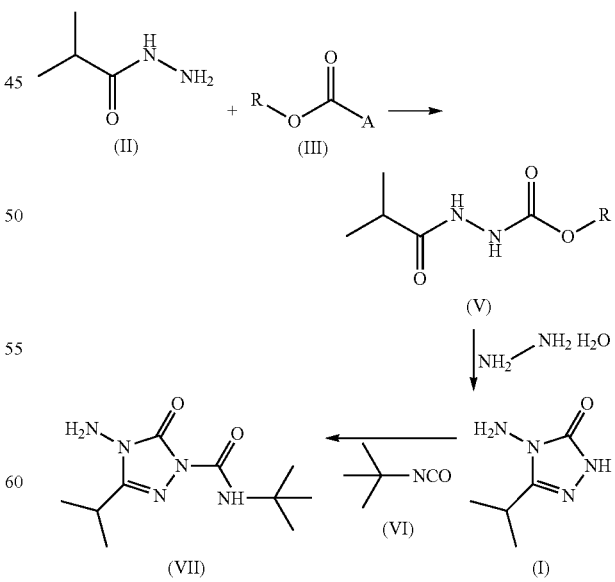

wherein A is Cl, F, Br, or OR, and R is a $C_1$ to $C_{12}$ alkyl group or aryl group.

Isobutyric acid hydrazide of Formula II used as a starting material in step (1) of the present invention is a known compound having the following formula.

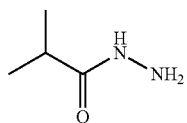

(II)

In the present invention, the isobutyric acid hydrazide was prepared with reference to Example 1 described in U.S. Pat. No. 5,756,752 (filed in 1997), and details of the preparation process thereof will be omitted herein.

In addition, a carbamating agent (carbamate) (—N—O—O) used as a starting material in step (1) of the method according to the present invention refers to a compound capable of producing carbamate using alkyl chloroformate (R—O—CO—Cl) or dialkyl carbonate. In the present invention, the carbamating agent may be alkyl chloroformate or dialkyl carbonate. In particular, a methyl group, an ethyl group, or an isopropyl group is most preferred in an alkyl group, and other groups may also be used. Alkyl chloroformate and dialkyl carbonate used in the present invention have the following Formulas III and IV, respectively:

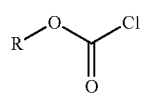

(III)

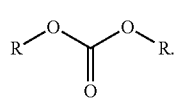

(IV)

Further, a functional group R of the dialkyl carbonate is preferably a methyl group and has the following Formula:

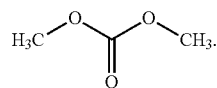

Further, the hydrazine carboxylic acid of following Formula V (also referred to as "2-(2-methyl-1-oxopropyl)-methyl ester") used in step (2) of the method according to the present invention has the following chemical structure and the hydrazine carboxylic acid obtained in step (1) may be directly used in step (2):

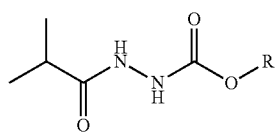

(V)

wherein R is an alkyl group such as methyl, ethyl, isopropyl, butyl, and the like.

Hydrazine hydrate used in step (2) of the method according to the present invention is generally mixed with a base compound (which can be dissolved in water in use) and a polar organic solvent at room temperature and the obtained mixture is heated to a desired reaction temperature. Then, the hydrazine carboxylic acid of Formula V obtained as an intermediate is slowly introduced into the heated reaction mixture, which in turn is maintained within a predetermined temperature range while being stirred as needed, until reaction is completed.

Lastly, t-butyl isocyanate used in step (2) of the method according to the present invention may be obtained by a preparation method known in the art, or may be a commercially available product, for example, products of Sigma-Aldrich. In addition, the base catalyst used in this process may include an organic amine, 1,8-diazabicyclo[5.4.0]undec-7-ene (DBU), an alkali salt such as LiOH, NaOH, KOH, and the like. Preferably, LiOH, NaOH, or KOH is used.

The reaction in the method according to the present invention is performed in the presence of a water soluble base compound. The base compound suitable for the present invention is a commercially available inorganic or organic base or a commercially available acid acceptor. Examples of the base compound may include alkali metal or alkaline earth metal acetates, amides, carbonates, hydrocarbon salts, hydrides, hydroxides, alkoxides, for example, sodium acetate, potassium acetate or calcium acetate, sodium carbonate, potassium carbonate, calcium carbonate, sodium hydrogen carbonate, potassium hydrogen carbonate, calcium hydrogen carbonate, lithium hydride, sodium hydride, calcium hydride, lithium hydroxide, sodium hydroxide, potassium hydroxide, calcium hydroxide, or sodium or calcium methoxide, ethoxide, or n- or i-propoxide, or n-, i-, s- or t-butoxide, and the like. As the base compound in performing the reaction in the method according to the present invention, alkali metal hydroxides such as lithium hydroxide, sodium hydroxide and potassium hydroxide are preferred. In particular, sodium hydroxide, which is capable of being dissolved in water, is more preferable.

The reaction in the method according to the present invention is performed in the presence of a polar organic solvent. Examples of the polar organic solvent may include sulfoxides such as dimethyl sulfoxide as well as dialkyl ethers (for example, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or diethyl ether, diethylene glycol dimethyl ether or diethyl ether); dialkyl ketones (for example, methylethylketone, methyl i-propyl ketone or methyl i-butyl ketone, nitriles (for example, acetonitrile, propionitrile, butyronitrile or benzonitrile); amides (for example, N,N-dimethyl-formamide (DMF), N,N-dimethyl-acetamide, N-methyl-formanilide, N-methyl-pyrrolidone or hexamethyl-phosphoramide); esters (for example, methyl, ethyl, n- or i-propyl, n-, i- or s-butyl acetate); and alcohols (for example, ethanol, n- or i-propanol, n-, i-, s- or t-butanol). As the alcohol used as a solvent in the reaction according to the present invention, methanol, ethanol, n- or i-propanol, n-, i-, s- or t-butanol is preferred.

Although the reaction in the method according to the present invention may be divided into step (1) corresponding to a carbamating reaction, step (2) corresponding to a cyclization reaction, and step (3) corresponding to a urea production reaction, steps (1), (2) and (3) may be continuously performed without separation and purification of the intermediate.

In the reaction of the method according to the present invention, a reaction temperature may be changed within a relatively wide range. Generally, step (1) corresponding to the carbamating reaction is performed at a reaction temperature of 0° C. to 60° C., and the reaction using alkyl chloroformate is performed at a reaction temperature of 0° C. to 30° C., preferably 10° C. to 25° C. In addition, the reaction using alkyl carbonate is performed at a reaction temperature of 50° C. to 70° C., preferably 55° C. to 65° C. Further, step (2) using hydrazine hydrate is performed at a reaction temperature of 50° C. to 150° C., preferably 70° C. to 130° C., more preferably 90° C. to 110° C. Last, step (3) using t-butyl isocyanate is performed at a reaction temperature of 30° C. to 100° C., preferably 50° C. to 80° C.

The reaction of the method according to the present invention is generally performed at normal pressure. However, the reaction of the method according to the present invention may be performed at an increased pressure or a decreased pressure, for example, 0.1 to 10 bars. In the case of using a low-boiling point alcohol, the reaction is preferably performed at an increased pressure.

With respect to a ratio of reactants used in step (1) of the method according to the present invention, the carbamating agent (III) or (IV) is used in an equivalent of 0.9 to 1.5 based on carbohydrazide (II). If the carbamating agent is used in an equivalent of less than 0.9, yield can be decreased, and if the carbamating agent is used in an equivalent of more than 1.5, impurity content can be increased or purification can become difficult, thereby causing deterioration in economic feasibility. Most preferably, the carbamating agent is used in an equivalent of 0.98 to 1.05. In addition, with respect to a range of the base used in the reaction, when chloroformate (III) is used together with an alkali metal, the chloroformate is used in an equivalent of 1.0 to 1.5 based on the carbamating agent. If the chloroformate is used in an equivalent of less than 1.0, impurity content can be increased or yield can be decreased, and if the chloroformate is used in an equivalent of more than 1.50, yield and purity can be deteriorated. Further, when dialkyl carbonate (IV) is used, the reaction may be performed even in a catalytic content, that is, in an equivalent of 0.1 to 1.0. If the dialkyl carbonate is used in an equivalent of less than 0.1, the reaction rate can be significantly slow, thereby deteriorating yield, and if the dialkyl carbonate is used in an equivalent of more than 1, side-reaction can occur, thereby causing deterioration in economic feasibility.

In the cyclization reaction corresponding to step (2), hydrazine hydrate may be used in an equivalent of 0.98 to 1.2 based on the intermediate of Formula V. If the hydrazine hydrate is used in an equivalent of 1 or less, yield can be deteriorated, and if the hydrazine hydrate is used in an equivalent of 1.2 or more, impurities can be produced, thereby causing deterioration in economic feasibility. Further, the base may be used in an equivalent of 0.01 to 1.0, preferably in an equivalent of 0.05 to 0.2 as a catalytic content. If the base is used in an equivalent of less than 0.05, the reaction rate can be slow and yield can be deteriorated. If the base is used in an equivalent of 1 or more, impurities can be produced, thereby causing deterioration in economic feasibility.

In the urea production reaction corresponding to step (3), t-butyl isocyanate may be used in an equivalent of 0.90 to 1.50 based on the intermediate of Formula I. If the t-butyl isocyanate is used in an equivalent of 0.99 or less, yield can be deteriorated, and if the hydrazine hydrate is used in an equivalent of 1.10 or more, impurities can be produced, thereby causing deterioration in economic feasibility. Further, the base catalyst may be used in an equivalent of 0.001 to 1.0, preferably in an equivalent of 0.005 to 0.03 as a catalytic content. If the base catalyst is used in an equivalent of less than 0.005, the reaction rate can be slow and yield can be deteriorated. If the base catalyst is used in an equivalent of 0.03 or more, impurities can be produced, thereby causing deterioration in economic feasibility.

Hereinafter, the present invention will be described in detail with reference to examples, but is not limited thereto. First, Examples 1 to 6 show a process of preparing hydrazine carboxylic acid, which is an intermediate using various carbamating agents and bases in the preparation method according to the present invention, and Examples 7 and 9 show a process of preparing amino-triazolinone using the intermediate obtained in Examples 1 to 6. Further, Examples 10 to 12 show a process of preparing final product using the intermediate of amino-triazolinone obtained in Examples 7 to 9.

MODE FOR INVENTION

Example 1

Preparation of Intermediate Using Methyl Chloroformate (MCF)/NaOH/MC

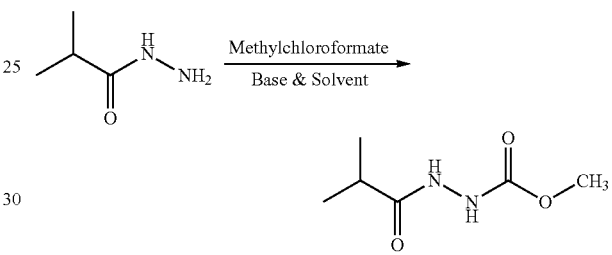

204 g (2.0 mole) of isobutyric acid hydrazide, 600 ml of methylene chloride (MC) and 170 g (2.1 mole) of 50% NaOH aqueous solution were mixed in a four-neck flask reactor equipped with a Dean-Stark trap. The obtained mixture was cooled to 10° C. or less and 190 g (1.0 equivalent) of methyl chloroformate (MCF) was slowly added to the mixture over 3 to 5 hours with strong stirring while slowly controlling temperature. After completion of addition, the resulting material was maintained at a reaction temperature ranging from 10° C. to room temperature to complete the reaction. After completion of the reaction, stirring was stopped, followed by layer separation to separate an organic layer (MC) placed at a lower portion of the flask reactor. The separated organic layer was washed with 600 ml of water twice. Then, the obtained organic layer was concentrated, whereby 314 g (yield: 98%) of hydrazine carboxylic acid (purity: 99.54 area % by HPLC) was obtained as an intermediate. The obtained intermediate could be directly used in subsequent reaction without additional purification and had a melting point of 81° C. to 89° C. FIG. 1 is a graph depicting H-NMR data of a product obtained in Example 1, and it could be seen that the analysis data was the same as data of a standard product (hydrazine carboxylic acid). The following shows NMR data thereof:

$^1$H-NMR (MeOD 400 MHz, d/ppm)1.133, 1.163 (d, 6H), 2.475 (q, 1H), 3.702 (s, 3H).

Example 2

Preparation of Intermediate Using Methyl Chloroformate (MCF)/NaOH/methanol 204 g (2.0 mole) of isobutyric acid hydrazide, 500 ml of methanol and 176 g (1.1 equivalents) of 50% NaOH aqueous solution were mixed in a four-neck flask reactor equipped with a Dean-Stark trap. The obtained mixture was cooled to 10° C. or less and 206 g (1.1 equivalents) of methyl chloroformate (MCF) was slowly added to the mixture over 3 to 5 hours with strong stirring while slowly controlling temperature. After completion of addition, the resulting material was maintained at a reaction temperature ranging from 10° C. to room temperature to complete the reaction. After completion of the reaction, the resulting material was crystallized through vacuum evaporation of methanol. After the obtained solid was filtered, the obtained cake was washed with water twice and dried. The obtained solid was a white solid and 292 g (yield: 91%) of hydrazine carboxylic acid (purity: 98.9 area % by HPLC) was obtained as an intermediate. The obtained solid could be directly used in subsequent reaction without additional purification.

Example 3

Preparation of Intermediate Using MCF/KOH/Methanol 102 g (1.0 mole) of isobutyric acid hydrazide, 300 ml of methanol and 145 g (1.05 equivalents) of 40% KOH aqueous solution were mixed in a four-neck flask reactor equipped with a Dean-Stark trap. The obtained mixture was cooled to 10° C. or less and 95 g (1.0 equivalent) of methyl chloroformate (MCF) was slowly added to the mixture over 2 to 3 hours with strong stirring while slowly controlling temperature. After completion of addition, the resulting material was maintained at a reaction temperature ranging from 10° C. to room temperature to complete the reaction. After completion of the reaction, the resulting material was crystallized through vacuum evaporation of methanol. After the obtained solid was filtered, the obtained cake was washed with water twice and dried. The obtained solid was a white solid and 142 g (yield: 88%) of hydrazine carboxylic acid (purity: 98.5 area % by GC) was obtained as an intermediate. The obtained solid could be directly used in subsequent reaction without additional purification.

Example 4

Preparation of Intermediate Using MCF/N,N-Triethylamine (TEA)

102 g (1.0 mole) of isobutyric acid hydrazide, 300 ml of methanol and 106 g (1.05 equivalents) of N,N-triethylamine (TEA) were mixed in a four-neck flask reactor equipped with a Dean-Stark trap. The obtained mixture was cooled to 10° C. or less and 95 g (1.0 equivalent) of methyl chloroformate (MCF) was slowly added to the mixture over 2 to 3 hours with strong stirring while slowly controlling temperature. After completion of addition, the resulting material was maintained at a reaction temperature ranging from 10° C. to room temperature to complete the reaction. After completion of the reaction, the produced triethylamine (TEA) hydrochloride was removed through filtration, and the resulting material was washed with weakly acidic water twice, followed by layer separation to separate an upper layer (toluene organic layer). The organic layer was crystallized through concentration. After the obtained solid was filtered, the obtained cake was washed with water twice and dried. The obtained solid was a white (pale yellow) solid and 136 g (yield: 85%) of hydrazine carboxylic acid (purity: 99.1 area % by GC) was obtained as an intermediate. The obtained solid could be directly used in subsequent reaction without additional purification.

Example 5

Preparation of Intermediate Using Ethyl Chloroformate (ECF)/NaOH

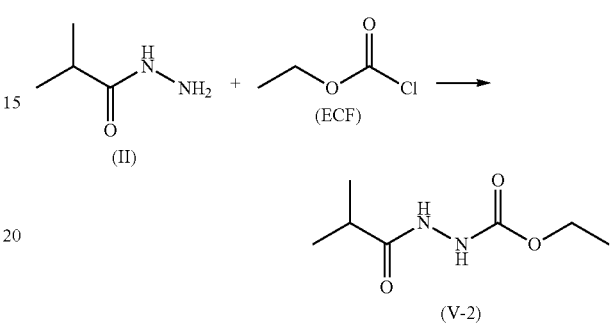

Figure 2:
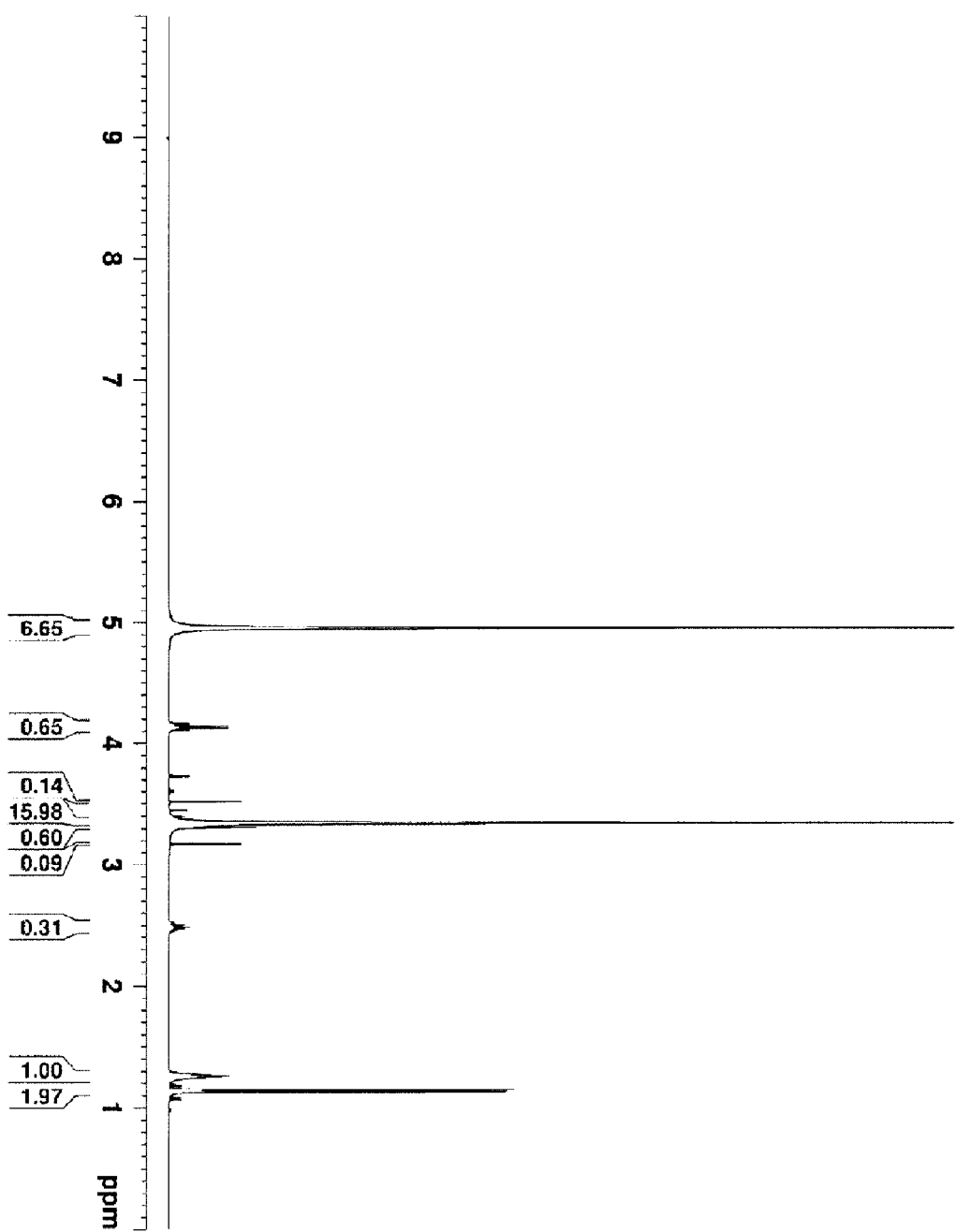
FIG. 2 is a graph depicting H-NMR data of a product obtained in Example 5.

30 g of isobutyric acid hydrazide, 300 ml of methanol and 34.3 g of $Na_2CO_3$ were mixed in a four-neck flask reactor equipped with a reflux condenser, followed by strong stirring and adjustment of the temperature to 15° C. to 20° C. Then, 33.5 g (1.05 equivalents) of ethyl chloroformate (ECF) was added to the mixture over 1 hour while maintaining the reaction temperature at 15° C. to 20° C., together with confirming the reaction completion. After completion of the reaction, unreacted $Na_2CO_3$ and NaCl were removed through filtration. Then, the solid obtained by concentration of the remaining liquid at reduced pressure was a pale yellow solid, and hydrazine carboxylic acid (purity: 98.39 area % by HPLC) was obtained substantially in a quantitative yield of 99% as an intermediate (V-2). The obtained intermediate could be directly used in subsequent reaction without additional purification. FIG. 2 is a graph depicting H-NMR data of a product obtained in Example 5, and it could be seen that the analysis data was the same as data of a standard product (hydrazine carboxylic acid). The following shows NMR data thereof:

$^1$H-NMR (MeOD 400 MHz, d/ppm)1.097, 1.148 (d, 6H), 1.278 (t, 3H), 2.486 (q, 1H), 4.146, 4.163 (q, 2H).

Example 6

Preparation of Intermediate Using Isopropyl Chloroformate (IPCF)

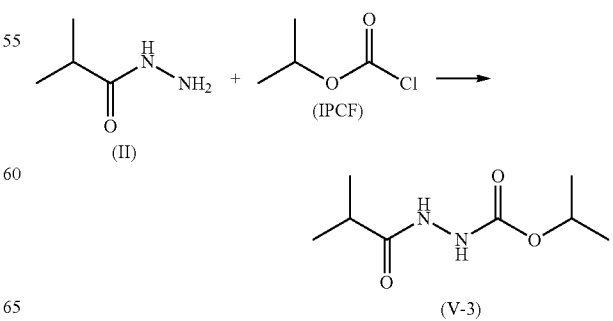

Figure 3:
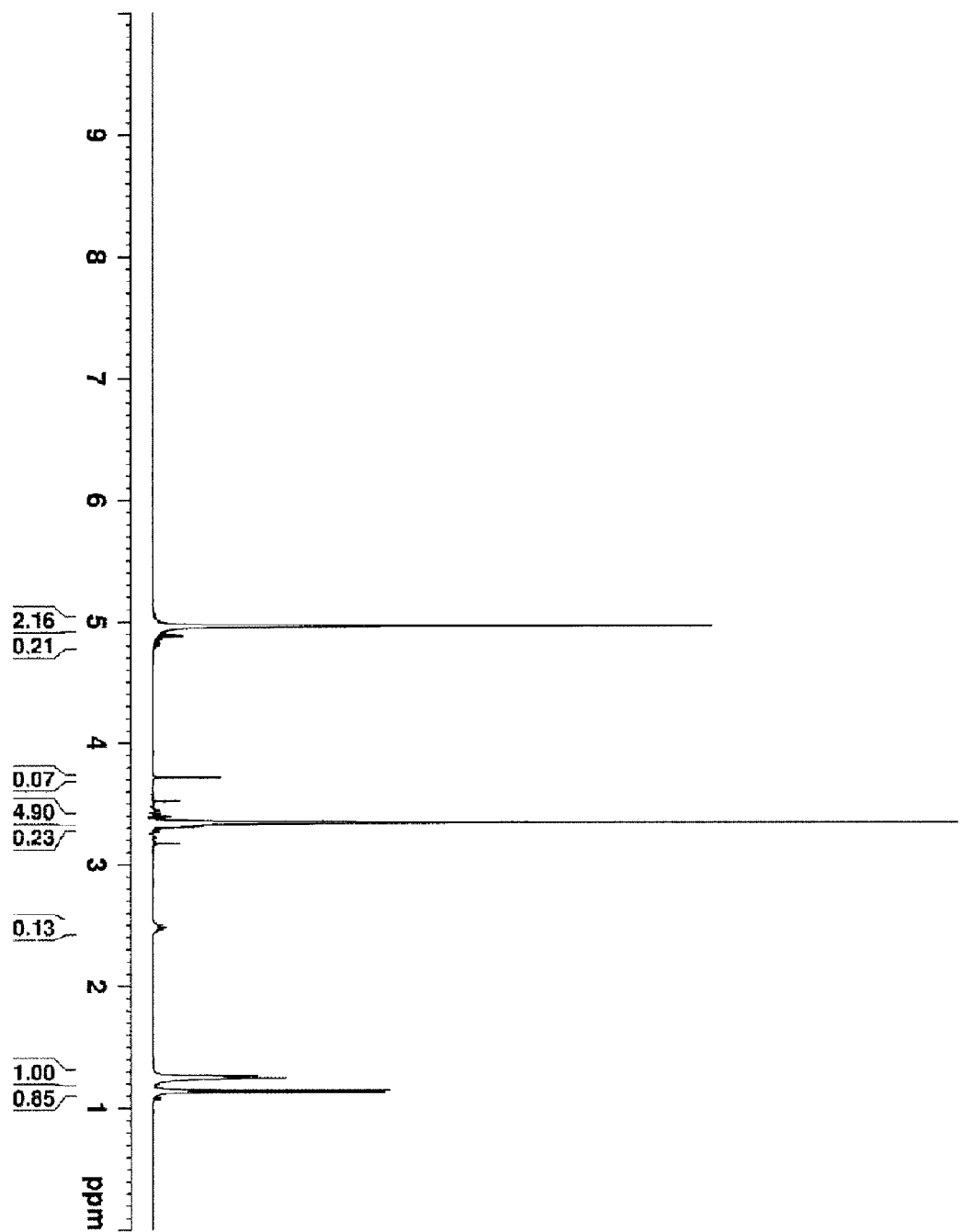
FIG. 3 is a graph depicting H-NMR data of a product obtained in Example 6.

30 g of isobutyric acid hydrazide, 240 ml of methanol and 34.3 g of Na$_2$CO$_3$ were mixed in a four-neck flask reactor equipped with a reflux condenser. Then, 37.8 g (1.05 equivalents) of isopropyl chloroformate (IPCF) was added to the mixture over 1 hour while maintaining the reaction temperature at 15° C. to 20° C., together with confirming the reaction completion. After completion of the reaction, NaCl produced as a side product and unreacted Na$_2$CO$_3$ were removed through filtration. Then, a product (V-3) was obtained substantially in a quantitative yield through concentration of the remaining liquid at reduced pressure and had a purity of 98.13% by HPLC. FIG. 3 is a graph depicting H-NMR data of the product obtained in Example 6, and it could be seen that the analysis data was the same as data of a standard product (hydrazine carboxylic acid). The following shows NMR data of the obtained product:

$^1$H-NMR (MeOD 400 MHz, d/ppm)1.31, 1.148 (d, 6H), 1.252 (m, 6H), 2.485 (q, 1H), 4.864 (q, 1H).

Example 7

Preparation of Amino-Triazolinone Using Toluene/NaOH

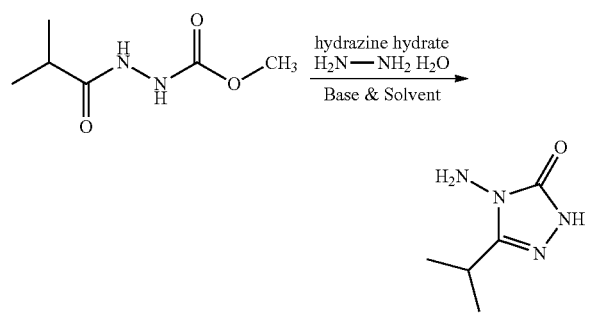

Figure 4:
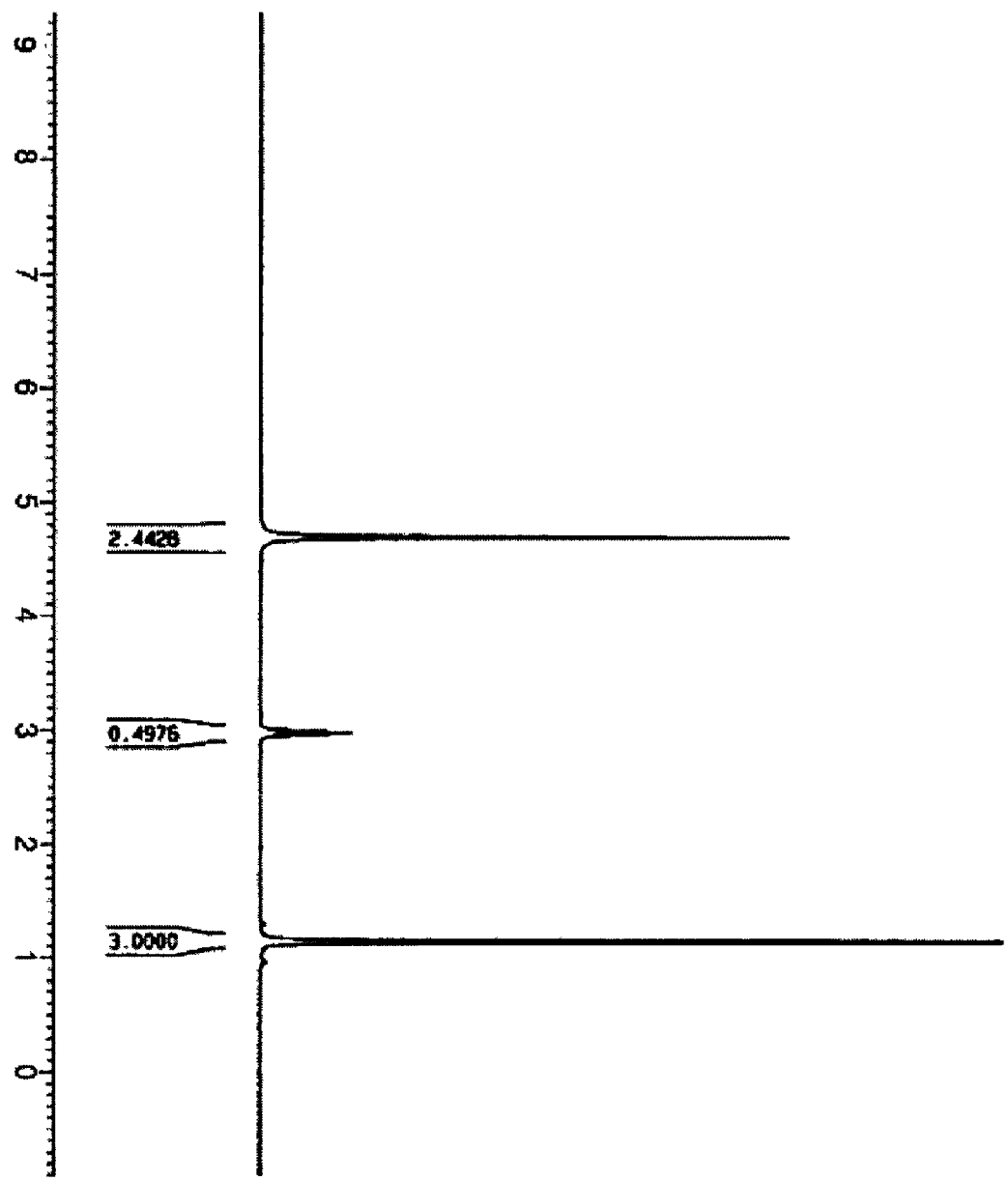
FIG. 4 is a graph depicting H-NMR data (D20, 400 MHz) of a product obtained in Example 7.
Figure 5:
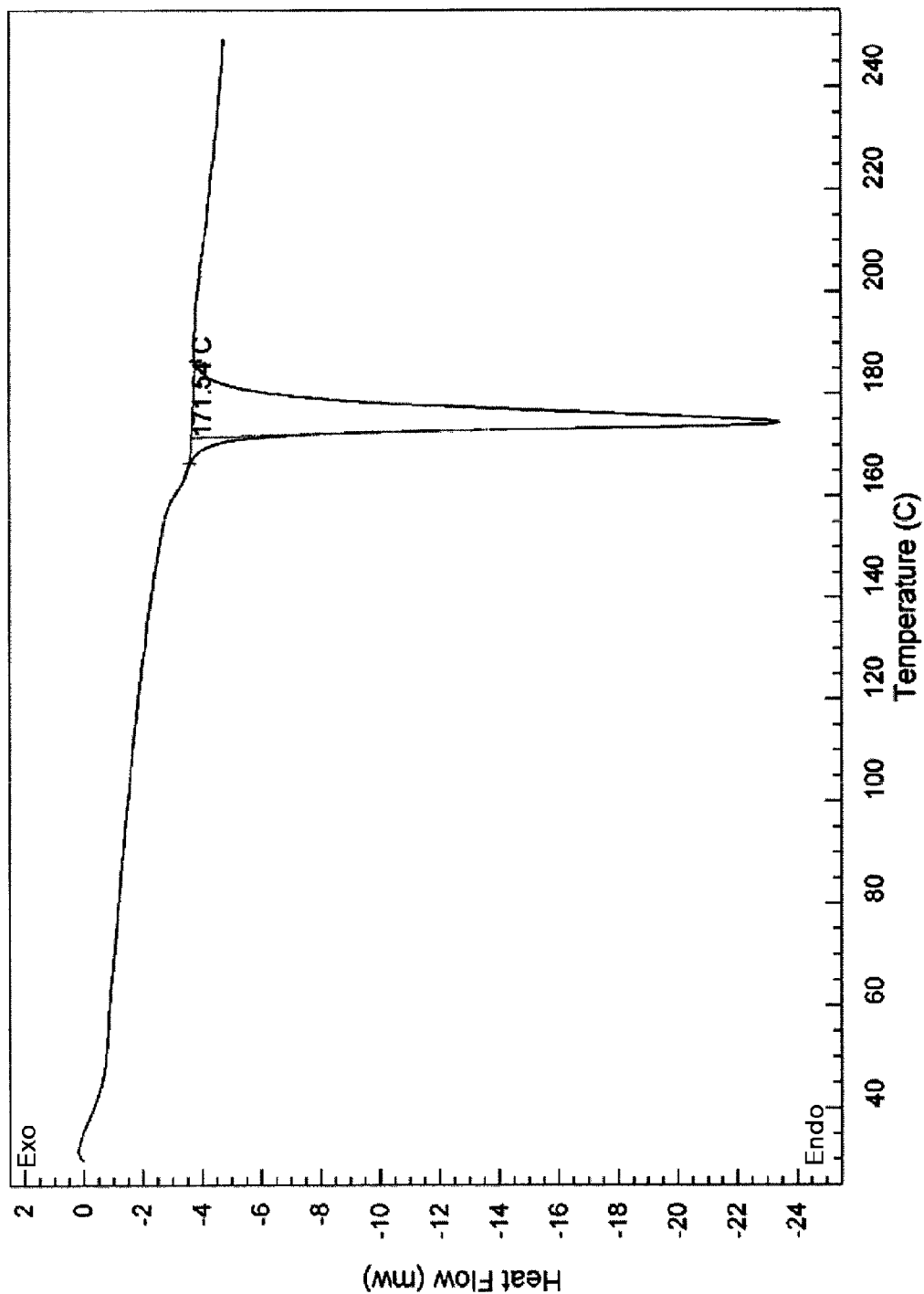
FIG. 5 is a graph depicting DSC (thermal analysis) data (D20, 400 MHz) for confirming a melting point of the product obtained in Example 7.

160 g (1.0 mole) of the intermediate (hydrazine carboxylic acid) prepared in Example 1, 300 ml of toluene, 51 g (1.0 mole) of hydrazine hydrate, and 0.15 mole of NaOH (45% aqueous solution) were added to a four-neck flask reactor equipped with a Dean-Stark trap, and the obtained mixture was refluxed at a reaction temperature of 100° C. to 110° C. while removing water produced as a side product. When there was no more water to be removed, the reaction was completed, followed by cooling the resulting material to room temperature while adding water to the resulting material, which in turn was crystallized at 10° C. Then, the crystallized product was neutralized (pH=7-7.5) with sulfuric acid and filtered, followed by washing the obtained cake with water and drying, thereby preparing 130 g of a product (yield: 91.4%, purity: 98% (by GC), melting point: 171.54° C.). FIG. 4 shows H-NMR data of the final product obtained in Example 7. It could be seen that the analysis data was the same as data of a standard intermediate (amino-triazolinone). In addition, FIG. 5 shows differential scanning calorimetry (DSC) (thermal analysis) data for confirming a melting point of the final product obtained in Example 7. It could be seen from the thermal analysis data that the obtained intermediate had a melting point of 171.54° C.

Example 8

Preparation of Amino-Triazolinone as Final Product Using Toluene/KOH 1.0 mole of the intermediate (hydrazine carboxylic acid) prepared in Example 5, 300 ml of toluene, 52.6 g (1.05 mole) of hydrazine hydrate, and 0.15 mole of KOH (40% aqueous solution) were added to a Dean-Stark reactor, and the obtained mixture was refluxed at a reaction temperature of 100° C. to 110° C. while removing water produced as a side product. After completion of the reaction, the resulting material was cooled to room temperature while adding water to the resulting material, which in turn was crystallized at 10° C. Then, the crystallized product was neutralized (pH=7-7.5) with sulfuric acid and filtered, followed by washing the obtained cake with water and drying, thereby preparing 127 g of a product (yield: 89.3%, purity: 99.2% (by GC), MP=171° C. to 175° C.).

Example 9

Preparation of Amino-Triazolinone as Final Product Using Toluene/KOH 1.0 mole of the intermediate (hydrazine carboxylic acid) prepared in Example 6, 300 ml of toluene, 52.6 g (1.05 mole) of hydrazine hydrate, and 0.15 mole of KOH (40% aqueous solution) were added to a Dean-Stark reactor, and the obtained mixture was refluxed at a reaction temperature of 100° C. to 110° C. while removing water produced as a side product. After completion of the reaction, the resulting material was cooled to room temperature while adding water to the resulting material, which in turn was crystallized at 10° C. Then, the crystallized product was neutralized (pH=7-7.5) with sulfuric acid and filtered, followed by washing the obtained cake with water and drying, thereby preparing 135 g of a product (yield 95.1%, purity 99.48% (by GC), MP=171.48° C.).

Example 10

Preparation of Amicarbazone as Final Product

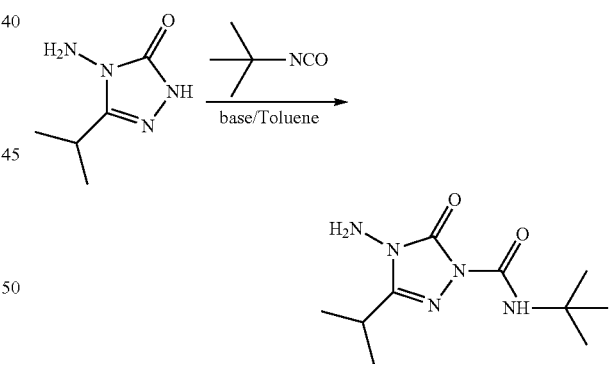

50 g of amino-triazolinone prepared in Example 7 and 220 g (about 250 ml) of toluene were mixed with stirring in a Dean-Stark reactor equipped with a stirrer, a reflux condenser and a thermometer, followed by adding 0.4 g of KOH (45%) thereto with stirring. Then, the reactor was heated and refluxed to remove water therefrom. After sufficient removal of water from the reactor, the interior temperature of the reactor was cooled to 60° C. and t-butyl isocyanate (TBIC) was added to the reactor using a dropping funnel over about 30 minutes.

Figure 6:
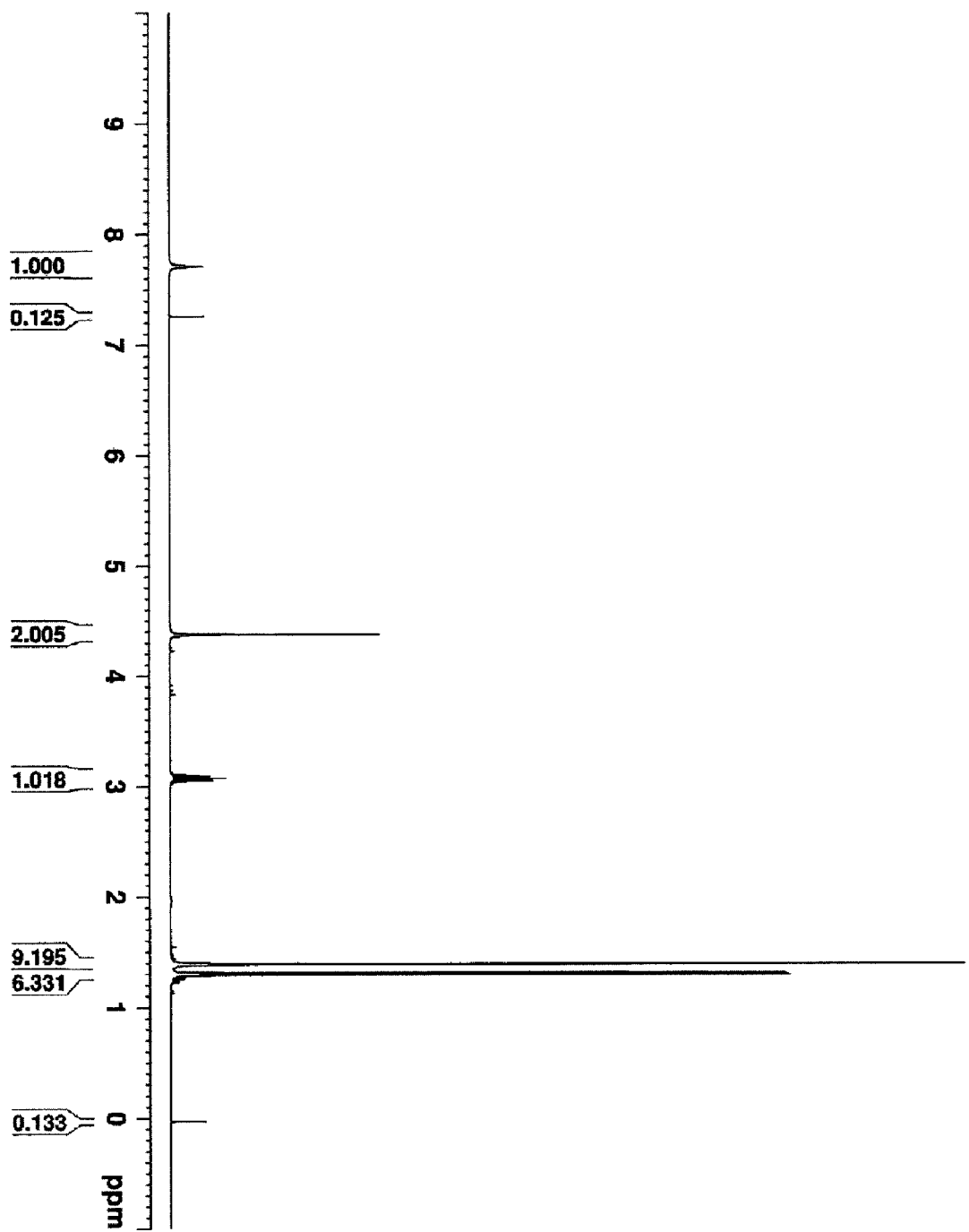
FIG. 6 is a graph depicting H-NMR data of a final product obtained in Example 10.

After completion of the reaction, the resulting material was cooled to 50° C. and neutralized with acid. The obtained product was slowly cooled to be crystallized. Here, in order to improve yield, the product was cooled to about −5° C. to −10° C. to be sufficiently crystallized, followed by filtering and drying, thereby preparing amicarbazone (yield: 93%, purity: 98% (HPLC)). FIG. 6 shows H-NMR data of the final product obtained in Example 10. It could be seen that the analysis data was the same as data of a standard final product. The following shows NMR data of the final product:

$^1$H-NMR(CDCl3 400 MHz, d/ppm)1.295, 1.312 (d, 6H), 1.390 (s, 9H), 3.076 (q, 1H), 4.377 (s, 2H), 7.715 (s, 1H).

Example 11

Preparation of Amicarbazone Using Intermediate of Example 8

50 g of amino-triazolinone prepared in Example 8 and 220 g (about 250 ml) of toluene were mixed with stirring in a Dean-Stark reactor equipped with a stirrer, a reflux condenser and a thermometer, followed by adding 0.4 g of KOH (45%) thereto with stirring. Then, the reactor was heated and refluxed to remove water therefrom. After sufficient removal of water from the reactor, the interior temperature of the reactor was cooled to 60° C. and t-butyl isocyanate (TBIC) was added to the reactor using a dropping funnel over about 30 minutes.

After completion of the reaction, the resulting material was cooled to 50° C. and neutralized with acid. The obtained product was slowly cooled to be crystallized. Here, in order to improve yield, the product was cooled to about −5° C. to 0° C. to be sufficiently crystallized, followed by filtering and drying, thereby preparing amicarbazone (yield: 95%, purity: 99.3% (HPLC)).

Example 12

Preparation of Amicarbazone Using Intermediate of Example 9

50 g of amino-triazolinone prepared in Example 9 and 220 g (about 250 ml) of toluene were mixed with stirring in a Dean-Stark reactor equipped with a stirrer, a reflux condenser and a thermometer, followed by adding 0.4 g of KOH (45%) thereto with stirring. Then, the reactor was heated and refluxed to remove water therefrom. After sufficient removal of water from the reactor, the interior temperature of the reactor was cooled to 60° C. and t-butyl isocyanate (TBIC) was added to the reactor using a dropping funnel over about 30 minutes.

After completion of the reaction, the resulting material was cooled to 50° C. and neutralized with acid. The obtained product was slowly cooled to be crystallized. Here, in order to improve yield, the product was cooled to about −5° C. to 0° C. to be sufficiently crystallized, followed by filtering and drying, thereby preparing amicarbazone (yield: 91%, purity: 99.5% (HPLC)).

The invention claimed is:

1. A method for preparing amicarbazone of the following Formula VII, comprising:
    (1) reacting acyl hydrazide of Formula II with a carbamating agent of Formula III to obtain hydrazine carboxylic acid of Formula V;
    (2) reacting the obtained hydrazine carboxylic acid of Formula V with hydrazine hydrate in the presence of a base catalyst to obtain a compound of Formula I; and
    (3) reacting the obtained compound of Formula I with t-butyl isocyanate of Formula VI in the presence of a base catalyst to prepare amicarbazone of Formula VII:

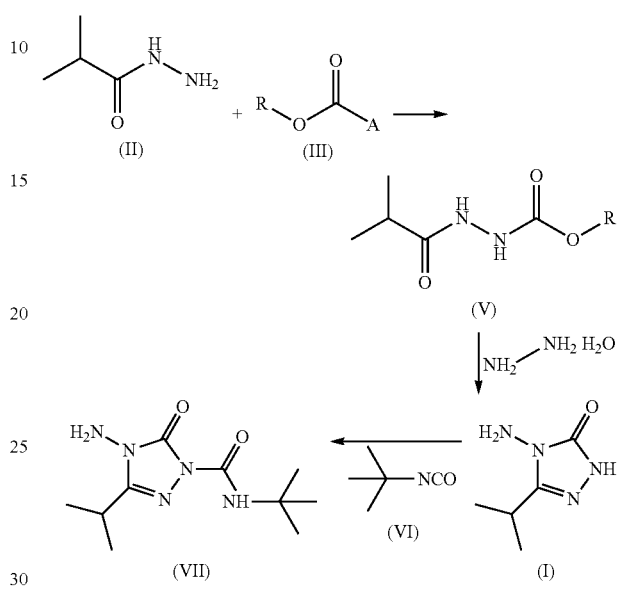

wherein A is Cl, F, Br, or OR, and R is a $C_1$ to $C_{12}$ alkyl group or aryl group.

2. The method according to claim 1, wherein the carbamating agent of Formula III is any one selected from the group consisting of methyl chloroformate, ethyl chloroformate, and isopropyl chloroformate.

3. The method according to claim 1, wherein the base catalyst is any one selected from the group consisting of LiOH, NaOH, KOH, LiHCO$_3$, Li$_2$CO$_3$, NaHCO$_3$, Na$_2$CO$_3$, KHCO$_3$, K$_2$CO$_3$, and CaCO$_3$.

4. The method according to claim 1, wherein the carbamating agent of Formula III used in step (1) is methyl chloroformate (MCF); wherein, in step (1), the acyl hydrazide of Formula II and the carbamating agent of Formula III are reacted in the presence of a solvent is selected from among methylene chloride, methanol and toluene; and a reaction temperature in step (1) ranges from 10° C. to 25° C.

5. The method according to claim 4, wherein the base catalyst used in step (2) is NaOH or KOH.

6. The method according to claim 4, wherein, in step (2), the hydrazine carboxylic acid of Formula V and the hydrazine hydrate are reacted in the presence of a solvent of toluene and the base catalyst, and a reaction temperature in step (2) ranges from 90° C. to 100° C.

7. The method according to claim 1, wherein the base catalyst used in step (3) is LiOH, NaOH, or KOH, and a reaction temperature in step (3) ranges from 50° C. to 80° C.

* * * * *